(12) United States Patent
Noh

(10) Patent No.: US 12,263,262 B2
(45) Date of Patent: Apr. 1, 2025

(54) APPARATUS FOR AUTOMATICALLY MANAGING THE HELMET

(71) Applicant: Jin Moon Noh, Gyeonggi-do (KR)

(72) Inventor: Jin Moon Noh, Gyeonggi-do (KR)

( * ) Notice: Subject to any disclaimer, the term of this patent is extended or adjusted under 35 U.S.C. 154(b) by 421 days.

(21) Appl. No.: 17/870,339

(22) Filed: Jul. 21, 2022

(65) Prior Publication Data

US 2023/0414801 A1 Dec. 28, 2023

(30) Foreign Application Priority Data

Jun. 27, 2022 (KR) .................... 10-2022-0078293

(51) Int. Cl.
*A61L 2/10* (2006.01)
*A42B 3/04* (2006.01)
*F26B 9/10* (2006.01)
*F26B 21/00* (2006.01)

(52) U.S. Cl.
CPC .............. *A61L 2/10* (2013.01); *A42B 3/0466* (2013.01); *F26B 9/10* (2013.01); *F26B 21/004* (2013.01)

(58) Field of Classification Search
CPC .......... A61L 2/10; A61L 2/24; A61L 2204/14; F26B 9/10; F26B 21/004
See application file for complete search history.

(56) References Cited

U.S. PATENT DOCUMENTS

2020/0103167 A1* 4/2020 Allen .................... F26B 21/004

FOREIGN PATENT DOCUMENTS

| CN | 111023788 A | * | 4/2020 |
| CN | 214120593 U | * | 9/2021 |
| KR | 20170014454 A | * | 2/2017 |
| KR | 10-1770090 B1 | | 8/2017 |
| KR | 10-1784593 B1 | | 10/2017 |
| KR | 10-1965064 B1 | | 4/2019 |
| KR | 10-2022-0042590 A | | 4/2022 |
| KR | 10-2022-0043273 A | | 4/2022 |
| KR | 10-2022-0047183 A | | 4/2022 |
| WO | WO-2021002741 A1 | * | 1/2021 ............. A42B 3/006 |

OTHER PUBLICATIONS

Office action issued on Mar. 1, 2024 from Korean Patent Office in a counterpart Korean Patent Application No. 10-2022-0078293 (English translation is also submitted herewith.).

* cited by examiner

*Primary Examiner* — David E Smith
(74) *Attorney, Agent, or Firm* — The PL Law Group, PLLC

(57) ABSTRACT

An apparatus according to an embodiment of the present disclosure is for automatically managing a helmet. Because the inside of a helmet may be sterilized and dried in a short time, a comfortable safety helmet may be ensured even during a short break time. Also, because charging may be performed without removing attachments such as an IoT device, an electronic device, and an illumination light from the helmet, the inconvenience of time and effort spent on attaching and detaching the attachments may be eliminated. Also, because the attachments such as the IoT device, the electronic device, and the illumination light may be charged at every break in the middle of work, a required capacity of a rechargeable battery may be reduced, a weight of the attachments may be reduced, and thus, the burden on the user to use the helmet may be reduced.

4 Claims, 6 Drawing Sheets

APPARATUS FOR AUTOMATICALLY MANAGING THE HELMET

CROSS-REFERENCE TO RELATED APPLICATION AND CLAIM OF PRIORITY

This application claims the benefit under 35 USC § 119 of Korean Patent Application No. 10-2022-0078293, filed on Jun. 27, 2022, in the Korean Intellectual Property Office, the entire disclosure of which is incorporated herein by reference for all purposes

BACKGROUND

1. Field

The present disclosure relates to an apparatus for automatically managing a helmet.

2. Description of the Related Art

A safety helmet holder or drying rack used in a general industrial site, sports, and leisure has only a mounting function or provides only a single function of, for example, sterilizing and drying serval safety helmets in a cabinet-type sterilizer.

Also, in order to sterilize and dry a safety helmet with such a product, an IoT device, an electronic device, an illumination light, etc. attached to the safety helmet should be removed and the helmet should be put into the product to use a sterilizing and drying function, and the IoT device, the electronic device, the lightening, etc. should be separately charged.

Accordingly, it is difficult to sterilize, dry, and charge the safety helmet during a short break time (30 minutes or less), and because the safety helmet may be sterilized, dried, and charged only after work or use, a required capacity of a rechargeable battery increases, and thus a weight increases.

SUMMARY

The present disclosure is directed to sterilizing and drying the inside of a helmet in a short time, to ensure a more comfortable safety helmet even during a short break time and improve user convenience.

Also, the present disclosure is directed to performing charging without removing attachments such as an IoT device, an electronic device, and an illumination light from the helmet, to eliminate the inconvenience of time and effort spent on attaching and detaching the attachments.

Also, the present disclosure is directed to enabling the attachments such as the IoT device, the electronic device, and the illumination light to be charged at every break in the middle of work, to reduce a required capacity of a rechargeable battery, reduce a weight of the attachments, and reduce the burden on a user to use the helmet.

Also, the present disclosure is directed to preventing people other than the user from using a device or arbitrarily taking the helmet through an ID recognition unit and a notification unit.

Objectives of the present disclosure are not limited thereto, and other objectives not mentioned will be clearly understood by one of ordinary skill in the art from the following description.

In one aspect, there is provided an apparatus for automatically managing a helmet, the apparatus including a holding rod provided on a front portion of a stand, having a plurality of vent holes in a top surface, and allowing a helmet to be mounted thereon, a blower fan located on the front portion of the stand to be disposed under the holding rod, and configured to generate an airflow and spray the airflow into the helmet through the plurality of vent holes, a guide member coupled to a rear portion of the stand in an upright position, a sensor provided on the guide member, the holding rod, or the stand, and configured to sense whether the helmet is mounted on the holding rod, and a controller configured to operate the blower fan when the sensor senses that the helmet is mounted on the holding rod.

The apparatus may further include a sterilizing light emitter located on the front portion of the stand to be disposed in the holding rod, and configured to emit sterilizing light into the helmet mounted on the holding rod, when the sensor senses that the helmet is mounted on the holding rod.

The apparatus may further include a charger provided on the guide member, and configured to perform wired or wireless charging when an object to be electrically charged is mounted.

The apparatus may further include an ID recognition unit provided on a front surface of the stand, and configured to recognize an ID indicator of a user, wherein the controller is configured to operate the blower fan or the sterilizing light emitter, when the sensor senses that the helmet is mounted on the holding rod and the ID recognition unit recognizes the ID indicator.

The apparatus may further include a notification unit provided on the stand or the guide member, and configured to generate a warning signal, wherein the controller is configured to, in a state where the ID recognition unit does not recognize the ID indicator after an operation of the blower fan or the sterilizing light emitter ends, when the sensor senses that the helmet is separated from the holding rod, control the notification unit to generate the warning signal.

According to an embodiment of the present disclosure, because the inside of a helmet may be sterilized and dried in a short time, a more comfortable safety helmet may be ensured even during a short break time and user convenience may be improved.

Also, because charging may be performed without removing attachments such as an IoT device, an electronic device, and an illumination light from the helmet, the inconvenience of time and effort spent on attaching and detaching the attachments may be eliminated.

Also, because the attachments such as the IoT device, the electronic device, and the illumination light may be charged at every break in the middle of work, a required capacity of a rechargeable battery may be reduced, a weight of the attachments may be reduced, and thus, the burden on a user to use the helmet may be reduced.

Also, people other than the valid user may be prevented from using a device or arbitrarily taking the helmet through an ID recognition unit and a notification unit.

DETAILED DESCRIPTION

Figure 1:
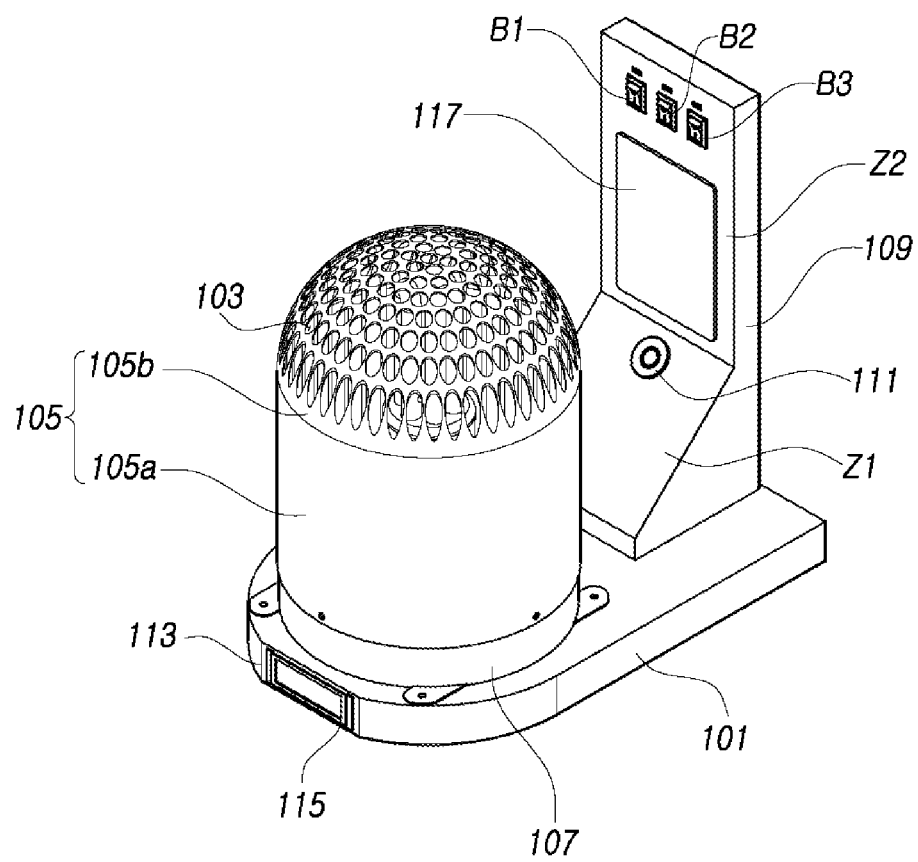
FIG. 1 is a perspective view illustrating an apparatus for automatically managing a helmet according to an embodiment of the present disclosure.

Hereinafter, some embodiments of the present disclosure will be described in detail through exemplary drawings. In adding reference numerals to elements of each drawing, it should be noted that the same elements are denoted by the same reference numerals as much as possible even when they are shown on different drawings. Also, in describing the present disclosure, detailed descriptions of related well-known functions or configurations that may blur the points of the present disclosure are omitted.

Also, in describing constituent elements of the present disclosure, the terms such as first, second, A, B, (a), and (b) may be used. These terms are intended to distinguish one element from another element, and only the essence, order, or sequence of the element is not limited thereto. It will be understood that when an element is referred to as being "connected", "coupled", or "accessed" to or by another element, the element may be directly connected, coupled, or accessed to or by the other element or intervening elements may be present.

Figure 2:
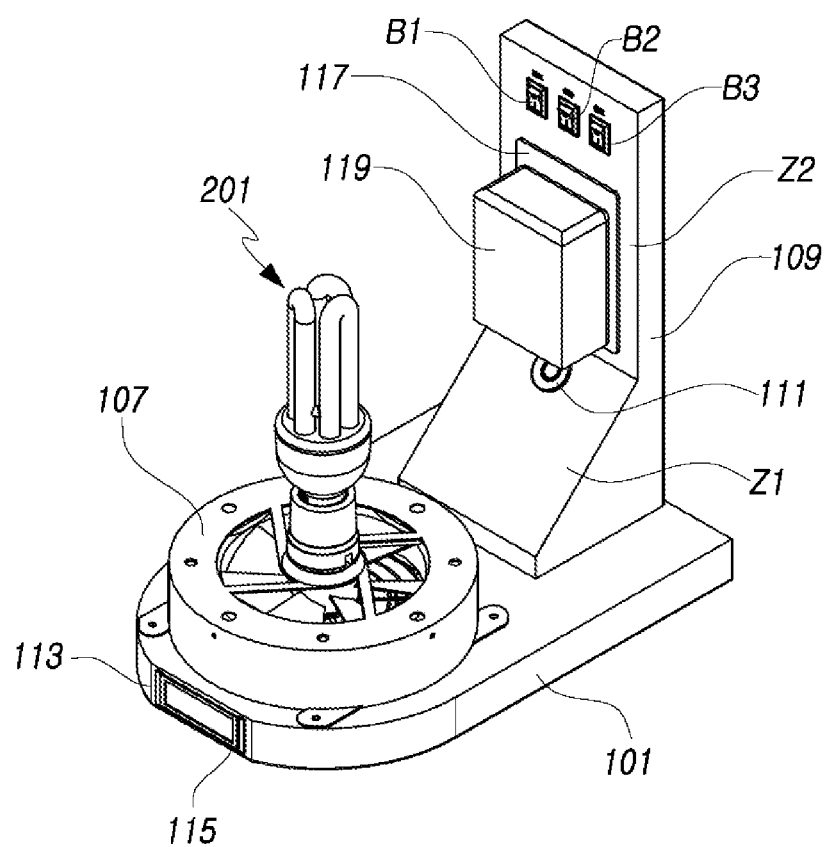
FIG. 2 is a perspective view illustrating a state in which a holding rod is removed in FIG. 1 and an object to be electrically charged is mounted.
Figure 3:
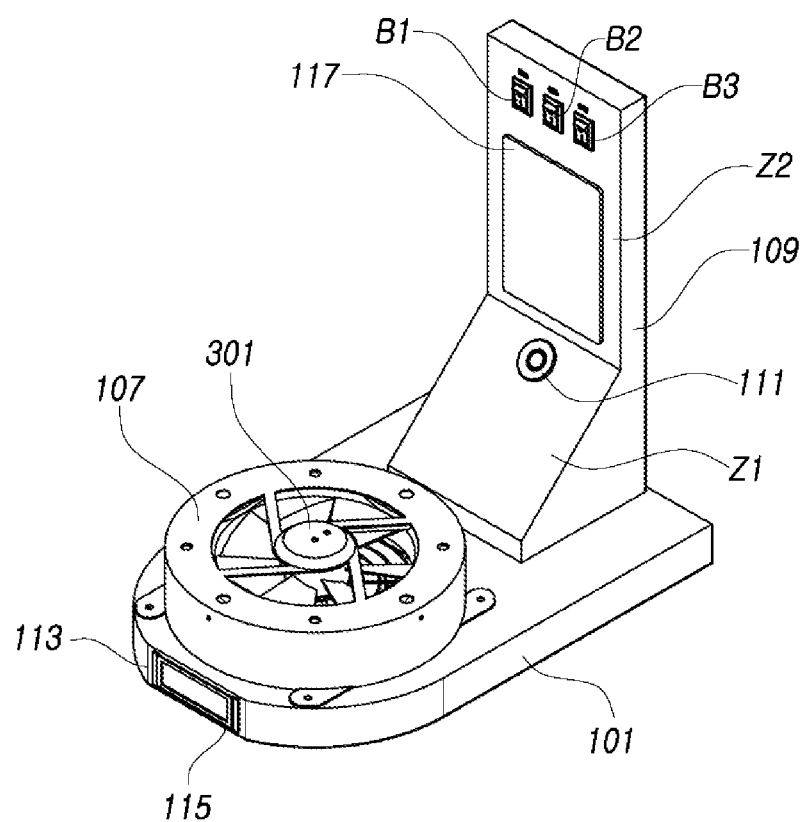
FIG. 3 is a perspective view illustrating a state in which a sterilizing light emitter and an object to be electrically charged are removed in FIG. 2.
Figure 4:
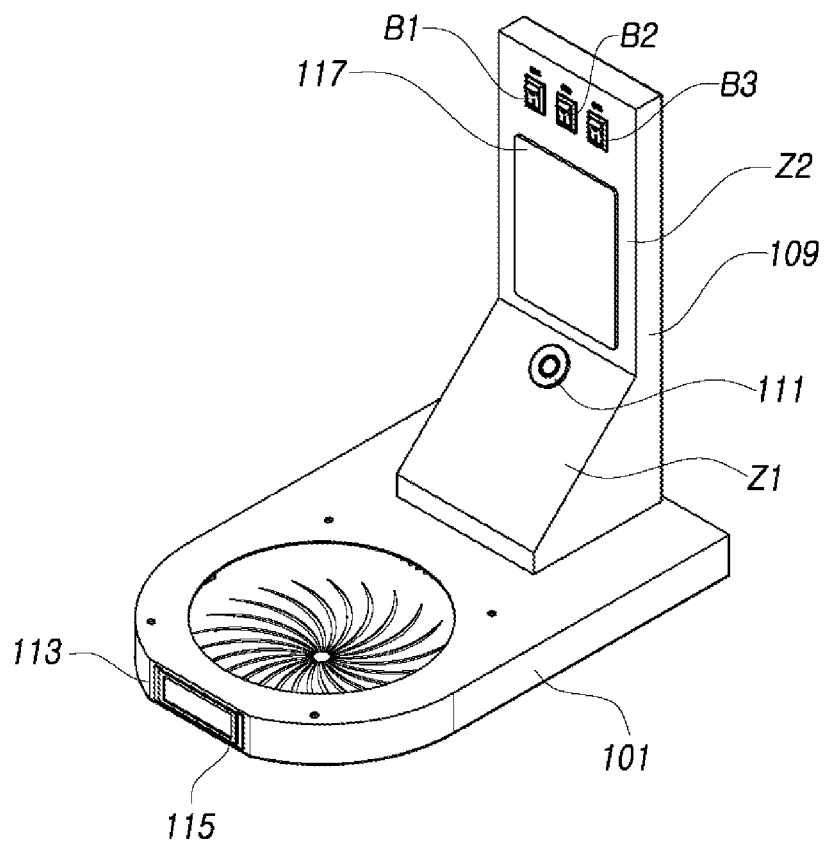
FIG. 4 is a perspective view illustrating a state in which a blower fan is removed in FIG. 3.
Figure 5:
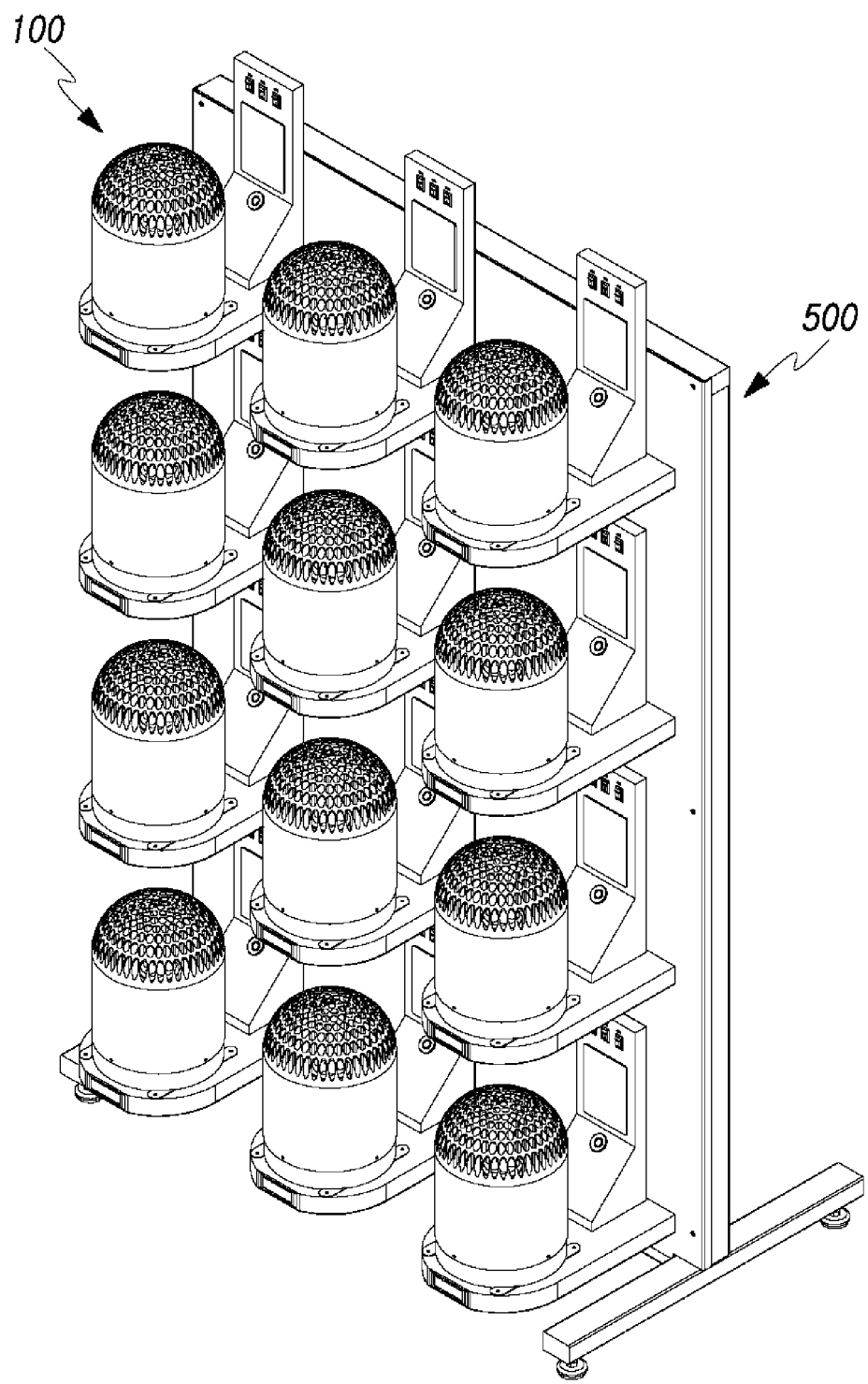
FIG. 5 is a perspective view illustrating an example in which a plurality of apparatuses for automatically managing helmets are provided on a mounting frame.
Figure 6:
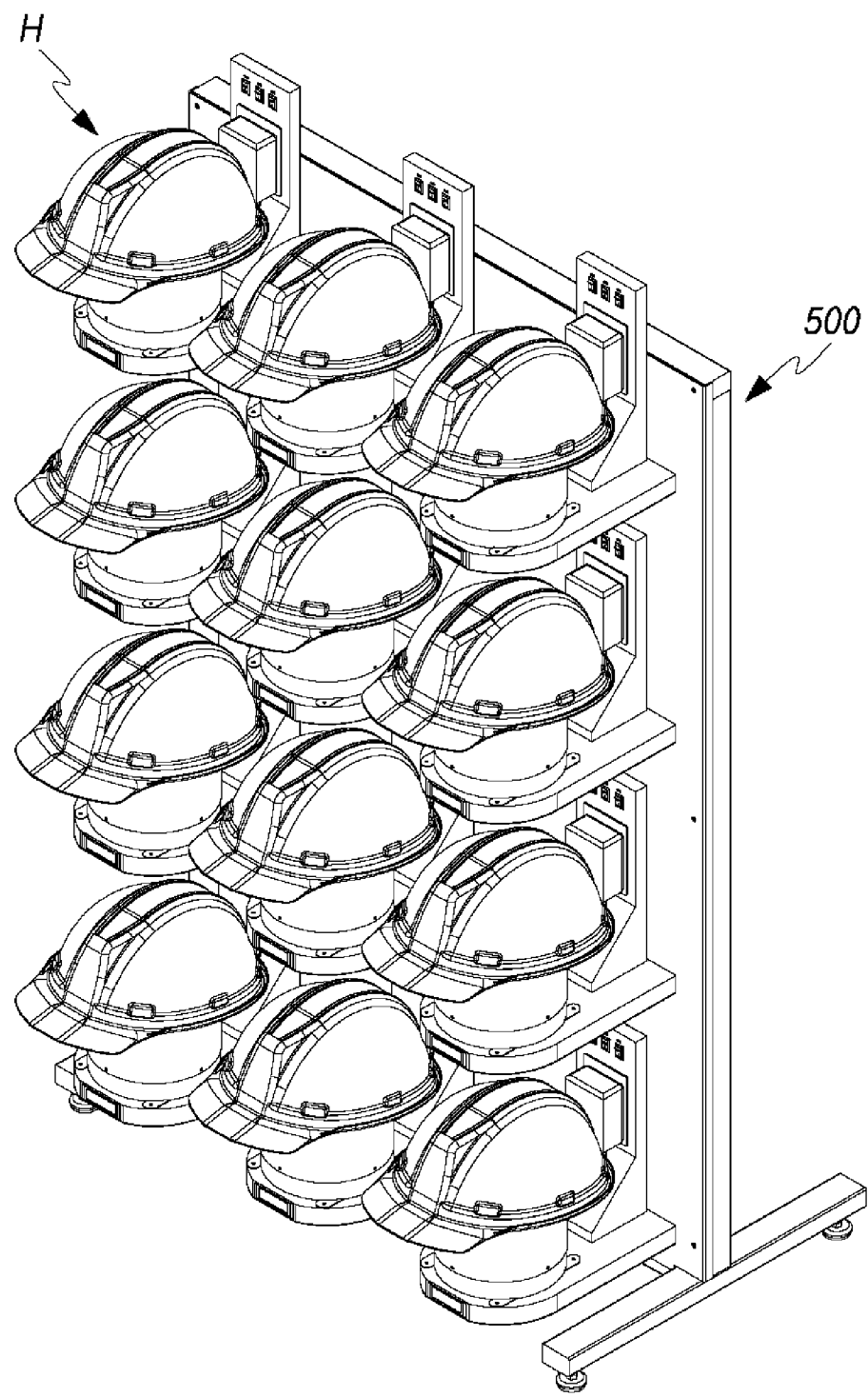
FIG. 6 is a perspective view illustrating a state in which a helmet is mounted on each apparatus for automatically managing a helmet in FIG. 5.

FIG. 1 is a perspective view illustrating an apparatus for automatically managing a helmet according to an embodiment of the present disclosure. FIG. 2 is a perspective view illustrating a state in which a holding rod is removed in FIG. 1 and an object to be electrically charged is mounted. FIG. 3 is a perspective view illustrating a state in which a sterilizing light emitter and an object to be electrically charged are removed in FIG. 2. FIG. 4 is a perspective view illustrating a state in which a blower fan is removed in FIG. 3. FIG. 5 is a perspective view illustrating an example in which a plurality of apparatuses for automatically managing helmets are provided on a mounting frame. FIG. 6 is a perspective view illustrating a state in which a helmet is mounted on each apparatus for automatically managing a helmet in FIG. 5.

As shown in the drawings, an apparatus 100 for automatically managing a helmet according to an embodiment of the present disclosure includes: a holding rod 105 provided on a front portion of a stand 101, having a plurality of vent holes 103 in a top surface, and allowing a helmet H to be mounted thereon; a blower fan 107 located on the front portion of the stand 101 to be disposed under the holding rod 105, and configured to generate an airflow and spray the airflow into the helmet H through the vent holes 103; a guide member 109 coupled to a rear portion of the stand 101 in an upright position; a sensor 111 provided on the guide member 109, the holding rod 105, or the stand 101, and configured to sense whether the helmet H is mounted on the holding rod 105; and a controller configured to operate the blower fan 107 when the sensor 111 senses that the helmet H is mounted on the holding rod 105.

Hereinafter, each element will be described in detail.

Stand 101

The stand 101 may be provided in a box shape with a space formed therein.

As shown in FIG. 4, a plurality of holes through which air flows are formed in a bottom surface of the stand 101.

Also, an ID recognition unit 113 described below may be provided on a front surface of the stand 101.

A name tag guide 115 into which a name tag (not shown) on which a user's name or the like is written is inserted may be provided on the front surface of the stand 101.

The name tag may be formed of a material (e.g., paper or plastic) that does not interfere with communication of the ID recognition unit 113 described below.

Electric wires for supplying electricity or transmitting control signals to the blower fan 107, the sensor 111, the controller, the ID recognition unit 113, a charger 117, a sterilizing light emitter 201, and operation buttons B1, B2, B3 are accommodated in the stand 101.

Electricity supplied to the electric wires may be transmitted from an external power source, and the external power source may be set to any of various power sources such as a typical electricity generation facility (power plant), a solar power generator, a wind power generator, or an energy storage system (ESS).

Holding Rod 105

The holding rod 105 is provided over the front portion of the stand 101.

The plurality of vent holes 103 are formed in the top surface of the hold rod 105.

The helmet H is mounted on the holding rod 105.

Examples of the helmet H include a safety helmet and a hat worn on the user's head.

The holding rod 105 includes: a housing 105a that has an empty inside, and is formed of an opaque material or allows an opaque material to be coated on a wall surface or an opaque film to be attached to the wall surface; and a cover 105b formed of a transparent material on the housing 105a and including the plurality of vent holes 103.

Because the housing 105a is opaque and the cover 105b is transparent, sterilizing light emitted by the sterilizing light emitter 201 described below is not emitted to a side surface of the housing 105a but is emitted only into the helmet H only through the cover 105b, thereby preventing the user from being exposed to the sterilizing light during a sterilization process of the helmet H.

The cover 105b may be provided in a hemispherical dome structure.

Blower Fan 107

The blower fan 107 is located on the front portion of the stand 101 to be disposed under the holding rod 105, and is configured to generate an airflow and spray the generated airflow into the helmet H through the vent holes 103 of the holding rod 105.

The blower fan 107 includes an electric motor, a blade, and a housing.

The blower fan 107 is selected in consideration of a noise level, an airflow amount, an expected lifetime, and cost-effectiveness.

Guide Member 109

The guide member 109 is coupled to the rear portion of the stand 101 in an upright position.

The guide member 109 functions as a housing in which the sensor 111, the charger 117, the operation buttons B1, B2, B3, and the controller described below are provided.

The guide member 109 may include: a lower area Z1 having an oblique surface on which the sensor 111 described below is provided; and an upper area Z2 extending upward from an upper end of the lower area Z1 and having a flat surface on which the charger 117 and the operation buttons B1, B2, B3 described below are provided.

Sensor 111

The sensor 111 is provided on the guide member 109, the holding rod 105, or the stand 101.

In the drawings, in particular, the sensor 111 is provided on the guide member 109.

The sensor 111 is configured to sense whether the helmet H is mounted on the holding rod 105.

For example, the sensor 111 may be an ultrasonic distance sensor, and a sensing distance may be, but is not limited to, 30 mm to 60 mm.

When the sensor 111 is provided on the holding rod 105, for example, the sensor 111 may be coupled to a lower portion of the holding rod 105, to function as a weight sensor for sensing a load of the helmet H mounted on the holding rod 105.

Controller

The controller (not shown) is configured to operate the blower fan 107 when the sensor 111 senses that the helmet H is mounted on the holding rod 105.

The controller controls whether to operate the sterilizing light emitter 201 described below, and controls an overall operation of the apparatus 100 for automatically managing a helmet.

The controller may be provided in the guide member 109.

Ventilating Light Emitter 201

The sterilizing light emitter 201 is located on the front portion of the stand 101 to be disposed in the holding rod 105, and is configured to emit sterilizing light into the helmet H mounted on the holding rod 105, when the sensor 111 senses that the helmet H is mounted on the holding rod 105.

Whether to operate the sterilizing light emitter 201 is controlled by the controller described above.

The sterilizing light emitter 201 may be, for example, a lamp that emits ultraviolet (UV)-C light.

An ultraviolet wavelength range of the lamp may be, for example, 250 nm to 275 nm.

As shown in FIGS. 2 and 3, the sterilizing light emitter 201 may be electrically connected and coupled to a socket 301 provided at the center of the housing of the blower fan 107.

Charger 117

The charger 117 is provided on the guide member 109 and performs wired or wireless charging when an object to be electrically charged 119 is mounted.

The object to be electrically charged 119 may be an attachment such as an IoT device, an electronic device, or an illumination light attached to the helmet H, and the attachment device may include a rechargeable battery therein, or a rechargeable battery for supplying electricity to the attachment device may be separately detachably attached to the helmet H.

In FIGS. 1 and 2, for the object to be electrically charged 119, a rechargeable battery is separately attached to the helmet H.

Assuming that the charger 117 has a wireless charging function, when the user mounts the helmet H on the holding rod 105 while adjusting the rechargeable battery separately attached to the helmet H to face the charger 117, the rechargeable battery is automatically charged. Accordingly, the inconvenience of separating attachment devices from the helmet H in order to charge a rechargeable battery in the related art may be eliminated.

ID Recognition Unit 113

The ID recognition unit 113 is provided on the front surface of the stand 101, and recognizes the user's ID indicator.

The user's ID indicator may be an identification card, an access card, or the like, and is provided as an electronic card (e.g., a card displayed on a smartphone) or a real card.

A method by which the ID recognition unit 113 recognizes the user's ID indicator may be selected from among a radio frequency identification (RF ID) method, a barcode recognition method, and a near field communication (NFC) method.

The controller is configured to operate the blower fan 107 or the sterilizing light emitter 201, when the sensor 111 senses that the helmet H is mounted on the holding rod 105 and the ID recognition unit 113 recognizes the ID indicator.

Accordingly, people other than the valid user may be prevented from using the apparatus 100 for automatically managing a helmet.

The ID recognition unit 113 may determine whether a user is the valid user by accessing user data built in an external server or stored in a self-built database by wire or wirelessly and comparing data of the recognized ID indicator with the user data.

Notification Unit

A notification unit (not shown) is provided on the stand 101 or the guide member 109, and is configured to generate a warning signal.

For example, the notification unit may be a speaker to generate a warning signal as sound, or may be an illumination light to generate a warning signal as visual light.

In a state where the ID recognition unit 113 does not recognize the ID indicator after an operation of the blower fan 107 or the sterilizing light emitter 201 ends, when the sensor 111 senses that the helmet H is separated from the holding rod 105, the controller may control the notification unit to generate a warning signal.

Accordingly, people other than the valid user may be prevented from arbitrarily taking the helmet H from the apparatus 100 for automatically managing a helmet.

Operation Buttons B1, B2, B3

The operation buttons B1, B2, B3 are provided on an upper portion of the guide member 109.

For example, the operation button B1 has a function of turning on/off the blower fan 107, by turning on/off electricity supplied to the blower fan 107.

The operation button B2 has a function of turning on/off the sterilizing light emitter 201, by turning on/off electricity supplied to the sterilizing light emitter 201.

Also, the operation button B3 has a function of turning on/off the charger 117, by turning on/off electricity supplied to the charger 117.

In addition, the operation buttons B1, B2, B3 may be provided as switches in which display lamps are embedded, to display operation states of the operation buttons B1, B2, B3.

Alternatively, separate display lamps for displaying operation states of the operation buttons B1, B2, B3 may be provided on the guide member 109 or the stand 101.

The controller may control an overall operation of the apparatus 100 for automatically managing a helmet, in a state where all of the operation buttons B1, B2, B3 are turned on.

When the controller loses its function due to a failure or the like, the operation buttons B1, B2, B3 may have a function of manually operating the blower fan 107, the sterilizing light emitter 201, and the charger 117.

As shown in FIGS. 5 and 6, a plurality of apparatuses 100 for automatically managing helmets may be provided on a mounting frame 500.

Accordingly, a plurality of helmets H may be collectively dried, sterilized, or charged.

As described above, according to an embodiment of the present disclosure, because the inside of a helmet may be sterilized and dried in a short time, a more comfortable safety helmet may be ensured even during a short break time and user convenience may be improved.

Also, because charging may be performed without removing attachments such as an IoT device, an electronic device, and an illumination light from the helmet, the inconvenience of time and effort spent on attaching and detaching the attachments may be eliminated.

Also, because the attachments such as the IoT device, the electronic device, and the illumination light may be charged at every break in the middle of work, a required capacity of a rechargeable battery may be reduced, a weight of the attachments may be reduced, and thus, the burden on the user to use the helmet may be reduced.

Also, people other than the valid user may be prevented from using a device or arbitrarily taking the helmet through an ID recognition unit and a notification unit.

In the above, even when all constituent elements constituting the embodiments of the present disclosure have been described as being combined into one or operating in combination, the present disclosure is not necessarily limited thereto. That is, within the scope of the objectives of the present disclosure, all of the constituent elements may operate by being combined into one or more.

The above description is merely illustrative of the technical idea of the present disclosure, and one of ordinary skill in the art to which the present disclosure pertains will be able to make various modifications and variations without departing from the essential characteristics of the present disclosure. Accordingly, the embodiments of the present disclosure should be considered in descriptive sense only and not for purposes of limitation of the scope of the present disclosure. The scope of the present disclosure is defined not by the detailed description of the present disclosure but by the appended claims, and all differences within the scope will be construed as being included in the present disclosure.

What is claimed is:

1. An apparatus for automatically managing a helmet, the apparatus comprising:
    a holding rod provided on a front portion of a stand, having a plurality of vent holes in a top surface, and allowing a helmet to be mounted thereon;
    a blower fan located on the front portion of the stand to be disposed under the holding rod, and configured to generate an airflow and spray the airflow into the helmet through the plurality of vent holes;
    a guide member coupled to a rear portion of the stand in an upright position;
    a sensor provided on the guide member, the holding rod, or the stand, and configured to sense whether the helmet is mounted on the holding rod;
    a controller configured to operate the blower fan when the sensor senses that the helmet is mounted on the holding rod-; and
    a charger provided on the guide member and configured to perform wired or wireless charging when an object to be electrically charged is mounted.

2. The apparatus for automatically managing a helmet according to claim 1, further comprising a sterilizing light emitter located on the front portion of the stand to be disposed in the holding rod, and configured to emit sterilizing light into the helmet mounted on the holding rod, when the sensor senses that the helmet is mounted on the holding rod.

3. An apparatus for automatically managing a helmet, the apparatus comprising:
    a holding rod provided on a front portion of a stand, having a plurality of vent holes in a top surface, and allowing a helmet to be mounted thereon;
    a blower fan located on the front portion of the stand to be disposed under the holding rod, and configured to generate an airflow and spray the airflow into the helmet through the plurality of vent holes:
    a guide member coupled to a rear portion of the stand in an upright position:
    a sensor provided on the guide member, the holding rod, or the stand, and configured to sense whether the helmet is mounted on the holding rod;
    a controller configured to operate the blower fan when the sensor senses that the helmet is mounted on the holding rod;
    a sterilizing light emitter located on the front portion of the stand to be disposed in the holding rod, and configured to emit sterilizing light into the helmet mounted on the holding rod, when the sensor senses that the helmet is mounted on the holding rod; and
    an ID recognition unit provided on a front surface of the stand, and configured to recognize an ID indicator of a user,
    wherein the controller is configured to operate the blower fan or the sterilizing light emitter, when the sensor senses that the helmet is mounted on the holding rod and the ID recognition unit recognizes the ID indicator.

4. An apparatus for automatically managing a helmet, the apparatus comprising:
    a holding rod provided on a front portion of a stand, having a plurality of vent holes in a top surface, and allowing a helmet to be mounted thereon;
    a blower fan located on the front portion of the stand to be disposed under the holding rod, and configured to generate an airflow and spray the airflow into the helmet through the plurality of vent holes;
    a guide member coupled to a rear portion of the stand in an upright position;
    a sensor provided on the guide member, the holding rod, or the stand, and configured to sense whether the helmet is mounted on the holding rod;
    a controller configured to operate the blower fan when the sensor senses that the helmet is mounted on the holding rod;
    a sterilizing light emitter located on the front portion of the stand to be disposed in the holding rod, and configured to emit sterilizing light into the helmet mounted on the holding rod, when the sensor senses that the helmet is mounted on the holding rod;
    an ID recognition unit provided on a front surface of the stand, and configured to recognize an ID indicator of a user; and
    a notification unit provided on the stand or the guide member, and configured to generate a warning signal,
    wherein the controller is configured to operate the blower fan or the sterilizing light emitter, when the sensor senses that the helmet is mounted on the holding rod and the ID recognition unit recognizes the ID indicator,
    wherein the controller is configured to, in a state where the ID recognition unit does not recognize the ID indicator after an operation of the blower fan or the sterilizing light emitter ends, when the sensor senses that the helmet is separated from the holding rod, control the notification unit to generate the warning signal.

* * * * *